US010352946B2

(12) United States Patent
Nazareth et al.

(10) Patent No.: US 10,352,946 B2
(45) Date of Patent: *Jul. 16, 2019

(54) TEST KITS FOR ELECTRONIC ANALYTE ASSAYING

(71) Applicant: Church & Dwight Co., Inc., Princeton, NJ (US)

(72) Inventors: Albert R. Nazareth, Mercerville, NJ (US); Andy Sturman, San Diego, CA (US); Benedict Zin, San Diego, CA (US)

(73) Assignee: Church & Dwight Co., Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/419,209

(22) Filed: Jan. 30, 2017

(65) Prior Publication Data

US 2017/0138954 A1    May 18, 2017

Related U.S. Application Data

(63) Continuation of application No. 13/402,024, filed on Feb. 22, 2012, now Pat. No. 9,588,113.

(51) Int. Cl.
  *G01N 33/557* (2006.01)
  *G01N 33/74* (2006.01)
  (Continued)

(52) U.S. Cl.
  CPC ..... *G01N 33/689* (2013.01); *G01N 33/54386* (2013.01); *G01N 33/557* (2013.01);
  (Continued)

(58) Field of Classification Search
  None
  See application file for complete search history.

(56) References Cited

U.S. PATENT DOCUMENTS

| 4,769,613 A | 9/1988 | Sawata et al. |
| 4,827,191 A | 5/1989 | Chapman |

(Continued)

FOREIGN PATENT DOCUMENTS

| EP | 0291194 | 11/1988 |
| EP | 0653625 | 5/1995 |

(Continued)

OTHER PUBLICATIONS

Anonymous: "Clearblue Digital Pregnancy Test with Conception Indicator," SPD Swiss Precision Diagnosics GmbH, [online] Jul. 2008. (Year: 2008).*

(Continued)

*Primary Examiner* — Christopher Adam Hixson
*Assistant Examiner* — Michelle Adams
(74) *Attorney, Agent, or Firm* — Church & Dwight Co., Inc.

(57) ABSTRACT

An improved qualitative or semi-quantitative diagnostic test for low levels of any analyte, such as hCG, in a biological sample, such as urine. The test comprises of a test device containing reagents for the detection of the monitored analyte and an electronic reader that measures color development at a detection area of the device. The color development is converted to an electronic or digital signal. Improvements were made to the detection process to optimize the detection of a valid fluid front, increase the detection limit without compromising the reliability and accuracy of the test system, and improve the determination of test result validity.

15 Claims, 12 Drawing Sheets

(51) Int. Cl.
*G01N 35/00* (2006.01)
*G01N 33/68* (2006.01)
*G01N 33/543* (2006.01)

(52) U.S. Cl.
CPC ......... *G01N 33/74* (2013.01); *G01N 2333/59* (2013.01); *Y10T 436/200833* (2015.01); *Y10T 436/203332* (2015.01)

(56) References Cited

U.S. PATENT DOCUMENTS

| | | |
|---|---|---|
| 4,849,340 A | 7/1989 | Oberhardt |
| 4,963,498 A | 10/1990 | Hillman et al. |
| 5,047,351 A | 9/1991 | Makiuchi et al. |
| 5,141,850 A | 8/1992 | Cole et al. |
| 5,179,288 A | 1/1993 | Miffiu et al. |
| 5,194,865 A | 3/1993 | Mason et al. |
| 5,210,538 A | 5/1993 | Kuroiwa |
| 5,254,995 A | 10/1993 | Hantke |
| 5,316,727 A | 5/1994 | Suzuki et al. |
| 5,467,778 A | 11/1995 | Catt et al. |
| 5,522,255 A | 6/1996 | Neel et al. |
| 5,580,794 A | 12/1996 | Allen |
| 5,657,762 A | 8/1997 | Coley et al. |
| 5,679,584 A | 10/1997 | Mileaf et al. |
| 5,686,659 A | 11/1997 | Neel et al. |
| 5,795,543 A | 8/1998 | Poto et al. |
| 5,860,922 A | 1/1999 | Gordon et al. |
| 5,872,713 A | 2/1999 | Douglas et al. |
| 5,889,585 A | 3/1999 | Markart |
| 5,935,075 A | 8/1999 | Casscells et al. |
| 6,055,060 A | 4/2000 | Bolduan et al. |
| 6,069,011 A | 5/2000 | Riedel |
| 6,100,829 A | 8/2000 | Fredrickson et al. |
| 6,146,333 A | 11/2000 | Mcneirney et al. |
| 6,187,598 B1 | 2/2001 | May et al. |
| 6,194,222 B1 | 2/2001 | Buechler et al. |
| 6,222,619 B1 | 4/2001 | Herron et al. |
| 6,234,974 B1 | 5/2001 | Catt et al. |
| 6,315,955 B1 | 11/2001 | Klein |
| 6,319,676 B1 | 11/2001 | Nazarath et al. |
| 6,364,844 B1 | 4/2002 | Regas et al. |
| 6,454,726 B1 | 9/2002 | Catt et al. |
| 6,585,663 B1 | 7/2003 | Coley et al. |
| 6,613,580 B1 | 9/2003 | Chow et al. |
| 6,767,714 B2 | 7/2004 | Nazareth et al. |
| 6,830,731 B1 | 12/2004 | Buechler et al. |
| 6,927,064 B1 | 8/2005 | Catt et al. |
| 7,044,919 B1 | 5/2006 | Catt et al. |
| 7,214,542 B2 | 5/2007 | Hutchinson |
| 7,220,597 B2 | 5/2007 | Zin et al. |
| 7,239,394 B2 | 7/2007 | Sharrock et al. |
| 7,315,378 B2 | 1/2008 | Phelan et al. |
| 7,317,532 B2 | 1/2008 | Sharrock et al. |
| 7,534,393 B2 | 5/2009 | Catt et al. |
| 9,588,113 B2 * | 3/2017 | Nazareth .......... G01N 33/54386 |
| 2002/0123671 A1 | 9/2002 | Haaland |
| 2006/0246435 A1 | 11/2006 | Kempin et al. |
| 2010/0126881 A1 | 5/2010 | Diamond et al. |
| 2010/0172802 A1 | 7/2010 | Sharrock et al. |
| 2011/0027901 A1 | 2/2011 | Gaster et al. |
| 2011/0056264 A1 | 3/2011 | Kaplan et al. |
| 2011/0290673 A1 | 12/2011 | Diamond et al. |
| 2012/0015376 A1 | 1/2012 | Bornhop |

FOREIGN PATENT DOCUMENTS

| | | |
|---|---|---|
| EP | 0666473 A1 | 8/1995 |
| EP | 0723146 A1 | 7/1996 |
| EP | 1571451 A1 | 9/2005 |
| GB | 2460660 A | 9/2009 |
| WO | 1994016313 A2 | 7/1994 |
| WO | 1996000110 A1 | 1/1996 |
| WO | 1996022521 A1 | 7/1996 |
| WO | 1996022531 A1 | 7/1996 |
| WO | 1996027798 A1 | 9/1996 |
| WO | 1998000194 A2 | 1/1998 |
| WO | WO 9825143 A1 | 6/1998 |
| WO | WO 9958050 A1 | 11/1999 |
| WO | WO 0128101 A1 | 4/2001 |
| WO | WO 0210343 A2 | 12/2002 |
| WO | WO 03000127 A2 | 1/2003 |
| WO | WO 2009/147437 A1 | 12/2009 |

OTHER PUBLICATIONS

Adlercreutz et al. "The measurement of urinary steroid glucuronides as indices of the fertile period in women." J. Steroid Biochem. 17(6):695-702 (1982).

Clearblue® easy Fertility Monitor Instruction Booklet. (2007).

Communication pursuant to Rule 164(1) EPC—Supplementary European Search Report—for European Patent Application No. 13752396, dated Sep. 30, 2015, pp. 1-5, which corresponds to this pending application.

Extended Supplementary European Search Report for EP 13752396. 5, dated Jan. 14, 2016, pp. 1-15, which corresponds to this pending application.

Gougeon et al. "Age-related changes of the population of human ovarian follicles: increase in the disappearance rate of non-growing and early-growing follicles in aging women." Biol. Reprod. 50(3):653-663 (1994).

Notification of Transmittal of the International Search Report and the Written Opinion of the International Searching Authority from WIPO—International Searching Authority dated Jun. 18, 2013.

Patent Examination Report No. 2; for Australian Application No. 2013222512, pp. 1-3, dated Apr. 22, 2016, which corresponds to this current application.

Pearlstone et al. "Ovulation induction in women age 40 and older: the importance of basal follicle-stimulating hormone level and chronological age." Fertil. Steril. 58(4): 674-679 (1992).

Stovall et al. "Serum progesterone and uterine curettage in differential diagnosis of ectopic pregnancy." Fertil. Steril. 57(2):456-457 (1992).

The Practice Committee of the American Society for Reproductive Medicine. "Aging and infertility in women." Fertil. Steril. 82(Suppl 1):S102-106 (2004).

Toner et al. "Basal follicle-stimulating hormone level is a better predictor of in vitro fertilization performance than age." Fertil. Steril. 55(4):784-791 (1991).

Who. "Temporal relationships between indices of the fertile period." Fertil Steril. 39(5):647-655 (1983).

Anonymous: "Clearblue Digital Pregnancy Test with Conception Indicator" SPD Swiss Precision Diagnosis GmbH, [online] Jul. 2008.

Creinin Mitchell D et al: "Accuracy of 1,4-6,8 serum beta-human chor1on1c gonadotropin cutoff values at 42 and 49 days' gestation" American Journal of Obstetrics and Gynecology, vol. 185, No. 4, Oct. 2001 (Oct. 2001), pp. 966-969.

Kadar Nicholas et al: A prospective, randomized study of the chorionic gonadotropin-time relationship in early gestation: Clinical implications, Fertility and Sterility, vol. 60, No. 3, 1993, pp. 409-412.

Lagrew D C et al: "Accuracy of Serum Human Chorionic Gonadotropin Concentrations and Ultrasonic Fetal Measurements in Determining Gestationalage" American Journal of Obstetrics and Gynecology, vol. 149, No. 2, 1984, pp. 165-168.

Lenton E A et al: "Plasma Concentrations of Human Chorionic Gonadotropin From the Time of Implantation Until the 2nd Week of Pregnancy"Fertility and Sterility, vol. 37, No. 6, 1982, pp. 773-778.

Westergaard et. al, Journal of Reproductive Medicine, 1985 vol. 30(1), pp. 57-60, "Single measurements of chorionic gonadotropin and schwangerschafts protein... " Abstract.

* cited by examiner

TEST KITS FOR ELECTRONIC ANALYTE ASSAYING

CROSS-REFERENCE TO RELATED APPLICATIONS

This application is a continuation application of U.S. Ser. No. 13/402,024 filed Feb. 22, 2012, the disclosure of which is hereby expressly incorporated by reference in its entirety.

BACKGROUND OF THE INVENTION

Field of the Invention

The present invention relates generally to diagnostic assays for analytes in a fluid sample. In particular, the invention relates to devices, methods, and test kits for detecting an analyte in a bodily fluid.

Description of the Related Art

Detection of human chorionic gonadotropin (hCG) in urine samples is routinely used to determine a woman's pregnant/non-pregnant status. Traditional one-step pregnancy test devices detect hCG by utilizing a double antibody system in a lateral flow format resulting in a "sandwich" complex of hCG, a capture antibody and a labeled antibody, which is captured at a specific detection area on a test strip. A digital version of the pregnancy test device consists of an opto-electronic reader powered by an internal battery that measures the absorbance/reflectance of the label particles specifically captured at the detection area of the test strip and automatically subtracts any non-specific background color from an adjacent area of the test strip that is outside the detection area. The adjusted measurement of absorbance/reflectance of accumulated label particles at the detection area is then compared to a preset threshold value and further processed into a clearly read YES+/PREGNANT or NO−/NOT PREGNANT digital result on a liquid crystal display (LCD) screen.

Although electronic readers provide the added convenience of eliminating the end-user step of interpreting the results of the test, a step required in traditional lateral flow devices, there is room for improvements. For an electronic reader system that incorporates a lateral flow test strip, one of the many challenges in increasing the detection sensitivity is the unpredictability of uneven migration of resolubilized reagents and sample flow which can affect the electronic interpretation of the test result resulting in an inaccurate test result determination. Unlike the lateral flow pregnancy test where the consumer merely looks for the presence of a line irrespective of its color intensity and its uniformity, in a digital pregnancy test it is extremely important that the test line is uniform in color intensity. However, this is not always possible due to the reasons cited above. Therefore, improved devices, methods, and test kits for electronic analyte assaying digital detection are desirable.

SUMMARY OF THE INVENTION

The devices, methods, and test kits described each have several aspects, no single one of which is solely responsible for its desirable attributes. Without limiting the scope of this disclosure as expressed by the claims which follow, some features will now be discussed briefly. After considering this discussion, and particularly after reading the section entitled "Detailed Description" one will understand how the features described provide advantages that include more accurate detection of an analyte through the use of a multi-factor process.

A method of detecting an analyte in a fluid sample is provided. The method includes receiving a fluid sample on an assay test device, generating a signal representative of reagent development during an assay time period, generating at least one reagent development trend signal during at least a portion of the assay time period, generating at least one endpoint signal representative of a final reagent development condition at or near the end of the assay time period, and generating an assay result output based at least in part on both the at least one reagent development trend signal and the at least one endpoint signal.

A device for detecting an analyte in a fluid sample is also described. The device includes means for collecting a fluid sample, means for generating a signal representative of reagent development during an assay time period, means for generating at least one reagent development trend signal during at least a portion of the assay time period, means for generating at least one endpoint signal representative of a final reagent development condition at or near the end of the assay time period, and means for generating an assay result output based at least in part on both the at least one reagent development trend signal and the at least one endpoint signal.

A test kit for detecting an analyte in a fluid sample is also provided. The test kit also includes a reader, wherein the reader includes an assay test device or a port for accepting an assay test device therein and a circuit. The circuit is configured to generate a signal representative of reagent development during an assay time period, generate at least one reagent development trend signal during at least a portion of the assay time period, generate at least one endpoint signal representative of a final reagent development condition at or near the end of the assay time period, and generate an assay result output based at least in part on both the at least one reagent development trend signal and the at least one endpoint signal.

A method of validating an analyte detection test from a fluid sample is also provided. The method includes applying a fluid sample to an assay test device, generating a signal representative of reagent development during an assay time period, generating at least one reagent development trend shape signal during at least a portion of the assay time period, and generating an invalid test output based at least in part on the reagent development trend shape signal.

An additional device for detecting an analyte in a fluid sample is provided. The device includes means for receiving a fluid sample, means for generating a signal representative of reagent development during an assay time period, means for generating at least one reagent development trend shape signal during at least a portion of the assay time period, and means for generating an invalid test output based at least in part on the reagent development trend shape signal.

Another test kit for detecting an analyte in a fluid sample is also provided. The test kit includes a reader. The reader includes an assay test device or a port for accepting an assay test device therein and a circuit. The circuit is configured to generate a signal representative of reagent development during an assay time period, generate at least one reagent development trend shape signal during at least a portion of the assay time period, and generate an invalid test output based at least in part on the reagent development trend shape signal.

Details of one or more implementations of the subject matter described in this specification are set forth in the accompanying drawings and the description below. Other features, aspects, and advantages will become apparent from the description, drawings, and claims. Note that the relative dimensions of the following figures may not be drawn to scale.

DETAILED DESCRIPTION OF THE INVENTION

Figure 1:
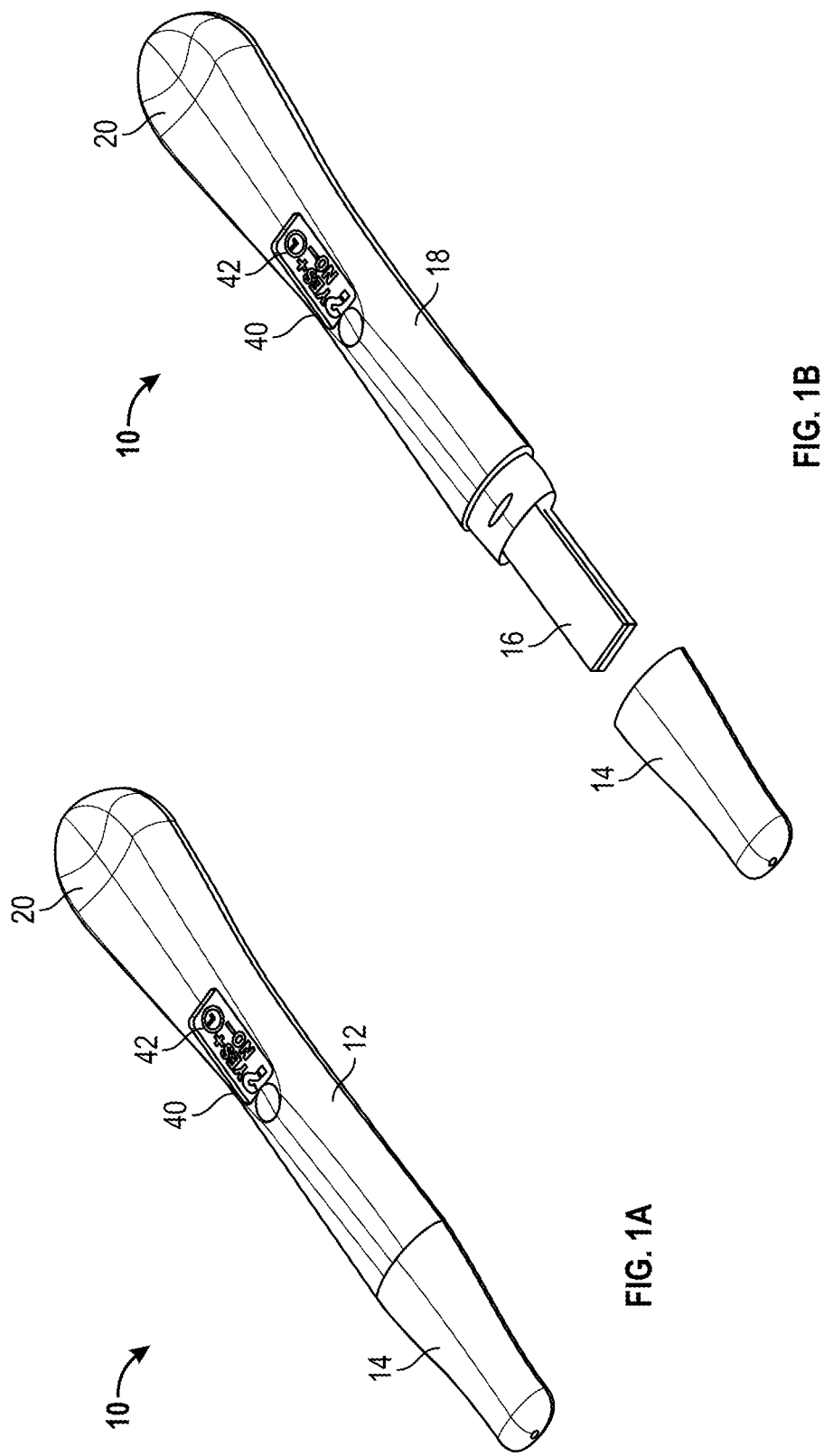
FIGS. 1A and 1B show perspective views of a digital detection device.

Various aspects of the novel apparatuses, test kits, and methods are described more fully hereinafter with reference to the accompanying drawings. The teachings disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the novel apparatuses, test kits, and methods disclosed herein, whether implemented independently of or combined with any other aspect of the invention. For example, an apparatus may be implemented or a method may be practiced using any number of the aspects set forth herein. In addition, the scope of the invention is intended to cover such an apparatus or method which is practiced using other structure, functionality, or structure and functionality in addition to or other than the various aspects of the invention set forth herein. It should be understood that any aspect disclosed herein may be embodied by one or more elements of a claim.

Although particular aspects are described herein, many variations and permutations of these aspects fall within the scope of the disclosure. Although some benefits and advantages of the preferred aspects are mentioned, the scope of the disclosure is not intended to be limited to particular benefits, uses, or objectives. Rather, aspects of the disclosure are intended to be broadly applicable to different detection technologies and device configurations some of which are illustrated by way of example in the figures and in the following description of the preferred aspects. The detailed description and drawings are merely illustrative of the disclosure rather than limiting, the scope of the disclosure being defined by the appended claims and equivalents thereof.

An improved diagnostic test that determines a woman's pregnant/non-pregnant status by detecting clinically significant and very low levels (e.g., 3-5 mIU/mL) of human chorionic gonadotropin (hCG) in urine. The test comprises a test strip containing reagents for the detection of hCG and an electronic reader that measures color development at a detection area of the test strip and converts it to an electronic or digital signal. Although the detection of hCG in urine is used to describe the invention, this disclosure is applicable to the qualitative or semi-quantitative detection of low levels of any analyte in a biological sample.

Improvements were made to the algorithm of the electronic reader to i) optimize the detection of a valid fluid front, ii) increase the detection limit without compromising the reliability and accuracy of the test system, and iii) improve the determination of test result validity.

FIGS. 1A and 1B show a perspective view of an exemplary digital detection device. The digital detection device 10 includes a cap 14. FIG. 1A illustrates a perspective view of the device 10 with the cap 14 intact, while FIG. 1B illustrates a perspective view of the device 10 with the cap 14 removed. The device also comprises an outer, molded casing 12 which defines a hollow, elongate enclosure. Casing 12 is configured to provide a recessed portion 20 shaped to permit users to place their thumb into the recessed portion and their forefinger on the bottom of the casing 12 to securely hold the device 10. A central section on the top of the casing 12 defines a centrally located window 40 which permits a user to observe test results. Inside the casing 12 is a lateral flow test strip and electronic components, details of which will be described further below. Casing 12 defines a sample receiving member 16 onto which a fluid sample can be applied to the test strip in the device 10. A removable cap 14 can be secured to one end of the casing enclosure over the sample receiving member 16. Sample receiving member 16 is positioned so that part of the sample receiving member is received in the casing enclosure and part of the sample receiving member 16 extends from the end of the casing enclosure. In this embodiment, color or reflectivity changes are sensed electronically, and the results are presented to a user on a display 42. The display 42 may render various icons or messages to a user, such as test results, device status, or error messages. The display 42 may be color or monochrome. In one embodiment, the display 42 is a liquid crystal display (LCD).

FIG. 2A shows another perspective view of an exemplary digital detection device without an integral test stick. A device 100 may be formed from plastic, metal, or other material. The device 100 includes a test stick acceptor port 110. The test strip acceptor port is designed to receive test sticks for analysis. The device 100 also includes a display 120. The display 120 may render various icons or messages to a user such as test results, device status, or error messages. The display 120 may be color or monochrome. In an example implementation, the display 120 may be a liquid crystal display (LCD). The device 100 may further include a test stick alignment marker 130. In the example shown, the test strip alignment marker 130 is a triangle pointing to the test stick acceptor 110. The test stick alignment marker aids with insertion of a test stick into the device 100. The device 100 may include a test stick ejector 140. The test stick ejector 140 may be a manual or electronic mechanism to eject a previously inserted test stick from the device 100.

FIG. 2B shows another perspective view of an exemplary digital detection device with a disposable test stick inserted therein. In the example shown, the device 100 is accepting a test stick assembly 200 housing the actual test strip 210. It is desirable for the test stick assembly 200 to couple with the device 100 so that the test stick assembly 200 will not fall out of the device 100 and may form a water resistant seal to protect a portion of the device 100 from fluid samples collected via the test stick assembly 200. The coupling should also minimize ambient light leakage into the device when testing is being performed on a test strip. Fluid samples collected via the test stick assembly 200 are generally urine, although depending on the test being performed, could be blood, sweat, tears, saliva, or any bodily fluid. An example test strip 210 will be described below in reference to FIG. 5. The test stick assembly includes a test stick housing 220. In an implementation, the test stick housing 220 may be formed from plastic. The test stick assembly 200 includes a test stick alignment marker 230 corresponding with the test stick alignment marker 130 on the device 100. The test stick assembly 200 may also include a clicking sound feature to indicate proper alignment and insertion into device 100.

Figure 2:
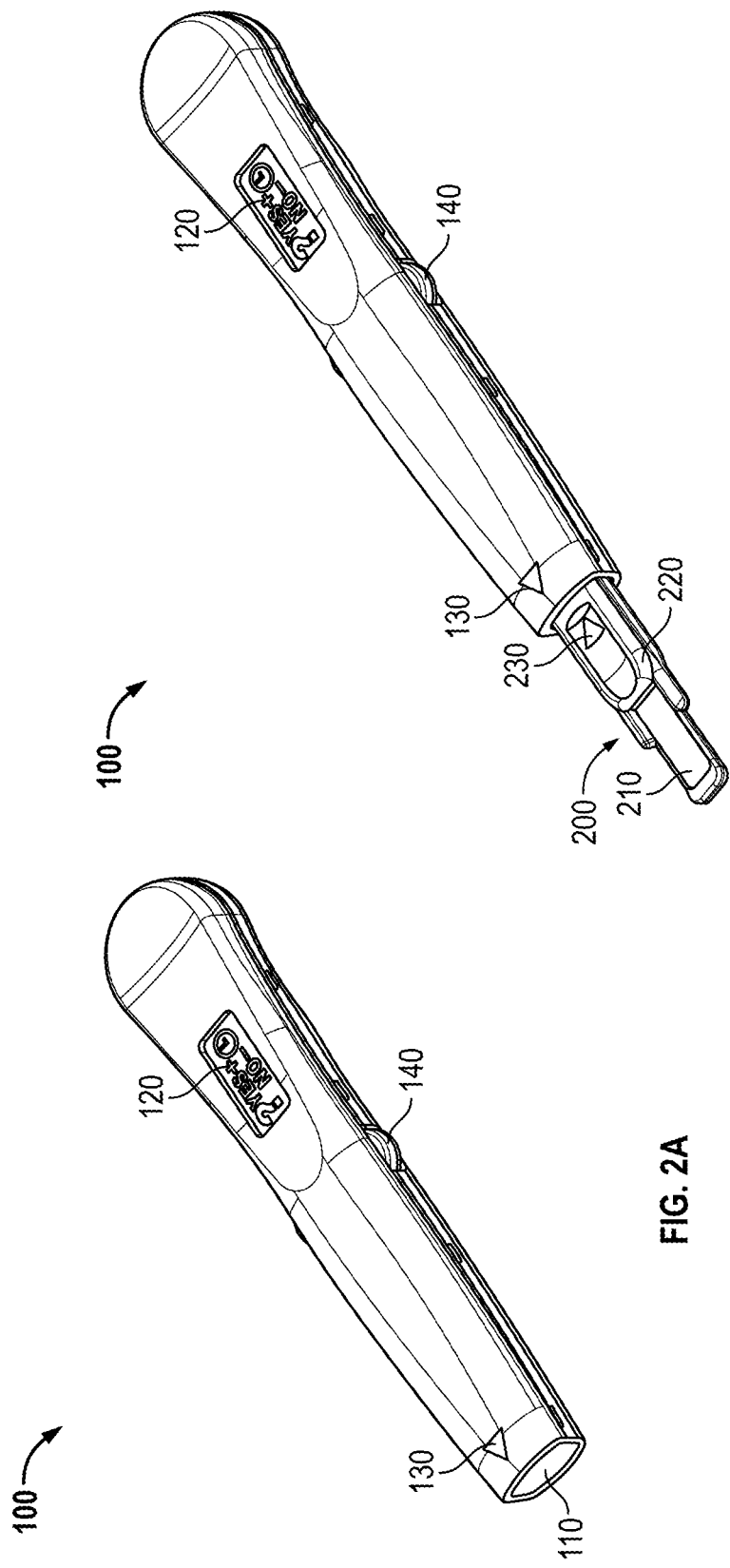
FIGS. 2A and 2B show perspective views of another digital detection device with a removable test stick.
Figure 3:
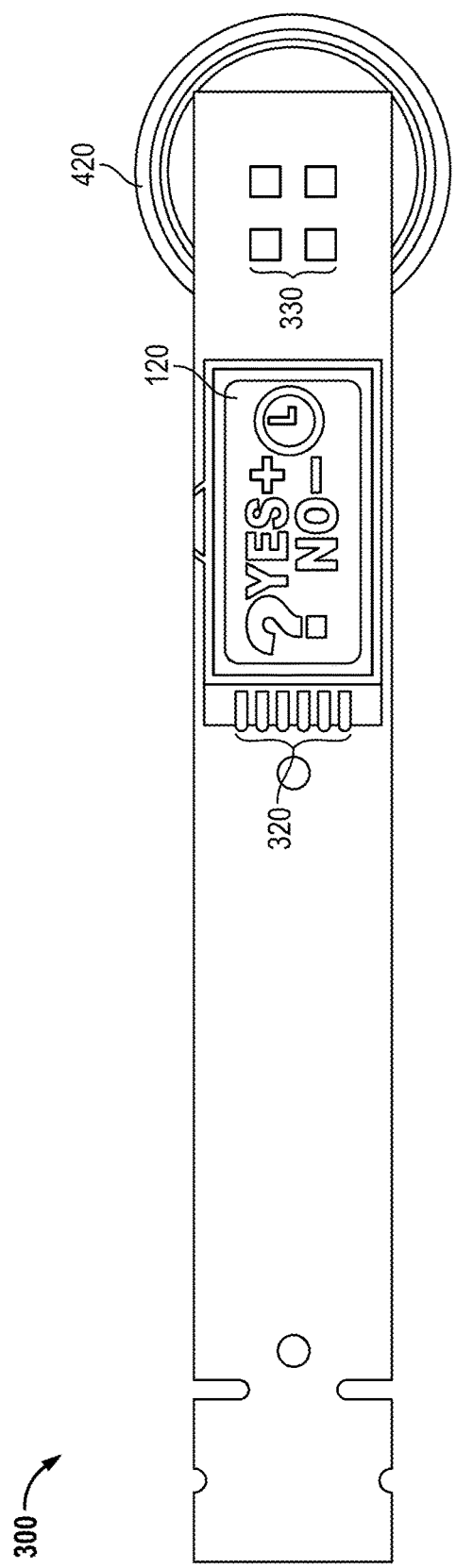
FIG. 3 is a top view of an example of a printed circuit board for an exemplary digital detection device.

FIG. 3 is a top view of an example of a printed circuit board for an exemplary digital detection device. The printed circuit board 300 may be housed, for example, in the digital detection devices of FIGS. 1A, 1B, 2A, and 2B. The display 120 is coupled with the printed circuit board 300 using one or more signal lines 320. The printed circuit board may include one or more input/output (I/O) terminals 330. The I/O terminals 330 may be used to read or write data from a memory (e.g., collected analyte readings, new program instructions, etc.). The memory may include volatile or non-volatile memory elements.

Figure 4:
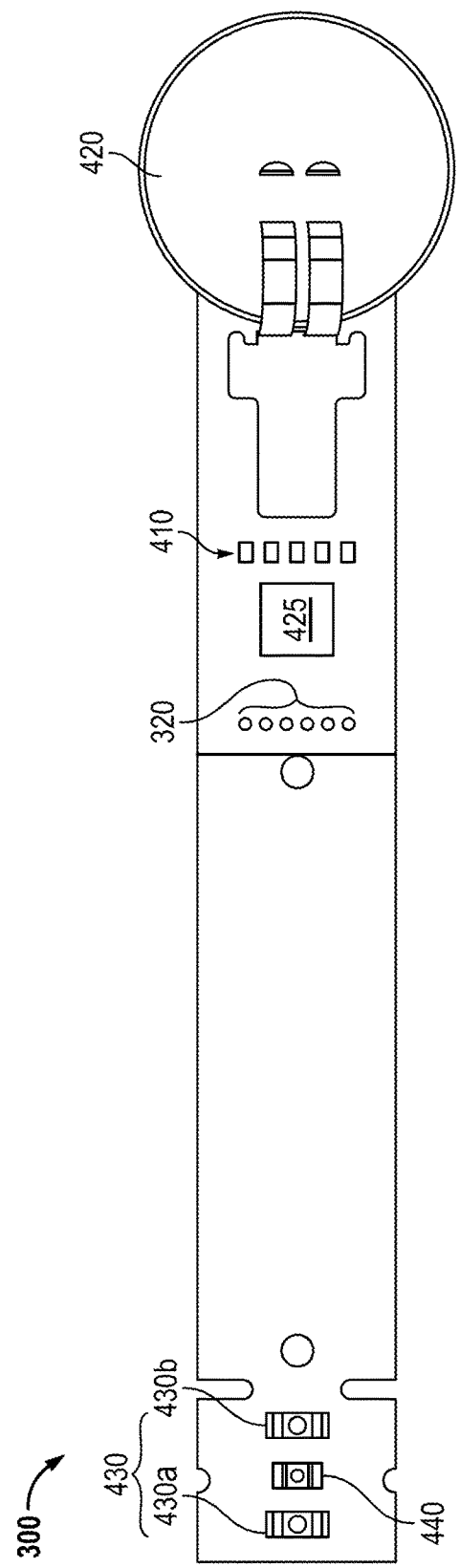
FIG. 4 is a bottom view of an example of a printed circuit board for an exemplary digital detection device.

FIG. 4 is a bottom view of an example of a printed circuit board for an exemplary digital detection device. More specifically, FIG. 4 is a bottom view of the printed circuit board 300 of FIG. 3. The printed circuit board 300 includes a processor chip 425 that may include digital circuitry such as a processor, memory, and input/output circuits, as well as analog to digital converters, digital to analog converters, analog circuits such as amplifiers, and may be implemented in whole or part in a microcontroller, programmable gate array, digital signal processor (DSP) or the like. The processor chip 425 is coupled with the display 120 and to one or more data I/O pads for test, data downloads, programming, etc. The memory may be used to store data received or produced by the processor chip 425. The memory may also be used to store instructions to direct operation of the processor chip 425. The printed circuit board 300 may further be coupled to a power source 420. In the example shown in FIG. 4, the power source is a battery, although any other suitable power source may be used. Discrete components such as resistors and capacitors 410 may also be provided on the printed circuit board 300.

The printed circuit board 300 includes one or more sensors 430. In the example shown in FIG. 4, the printed circuit board 300 includes two optical sensors 430a and 430b. In this implementation, the sensors 430 may be phototransistors. In other implementations, the sensors 430 may be one or more photodiodes, electroactive sensors, or radioactivity sensors. The sensors may be of the same or different types. The sensors 430 are coupled with the processor chip 425.

The printed circuit board 300 may include an emitter 440. In an implementation including photoelectric sensors 430, the emitter 440 may be a light source such as a light emitting diode (LED). In an implementation including photoelectric sensors 430, as shown for example in FIG. 4, the light source 440 may be located equidistant between the photoelectric sensors 430a and 430b. The light source 440 may be coupled with the processor chip 425. The light source 440 may illuminate according to a configurable pattern. In an implementation where the light source 440 is coupled with the processor chip 425, the illumination pattern may be controlled by the processor chip 425. In an implementation where the light source 440 is not coupled with the processor chip 425, the illumination pattern may be controlled by a separate timing circuit.

As the emitter 440 illuminates the test strip 210, the sensor 430 may detect a response from the illumination. For example, in an implementation where the emitter 440 is a light source, the photoelectric sensor 430 will detect the amount of light reflected by the test strip 210. An example method of detection will be discussed in more detail below.

The emitter 440 and sensor 430 may be used to detect the insertion of a test stick. When the digital detection device is not assembled with a test stick, the emitter in the digital detection device can turn on periodically, for example, every two seconds. Detection of the presence of a test stick may be achieved by detecting a large difference in sensor response depending on whether the emitter is on or off due to the presence of the nearby reflective surface of the test stick. The device 100 may use this information to alter operation mode (e.g., from low power stand-by mode in the packaging to higher power test mode when a test strip is inserted).

Figure 5:
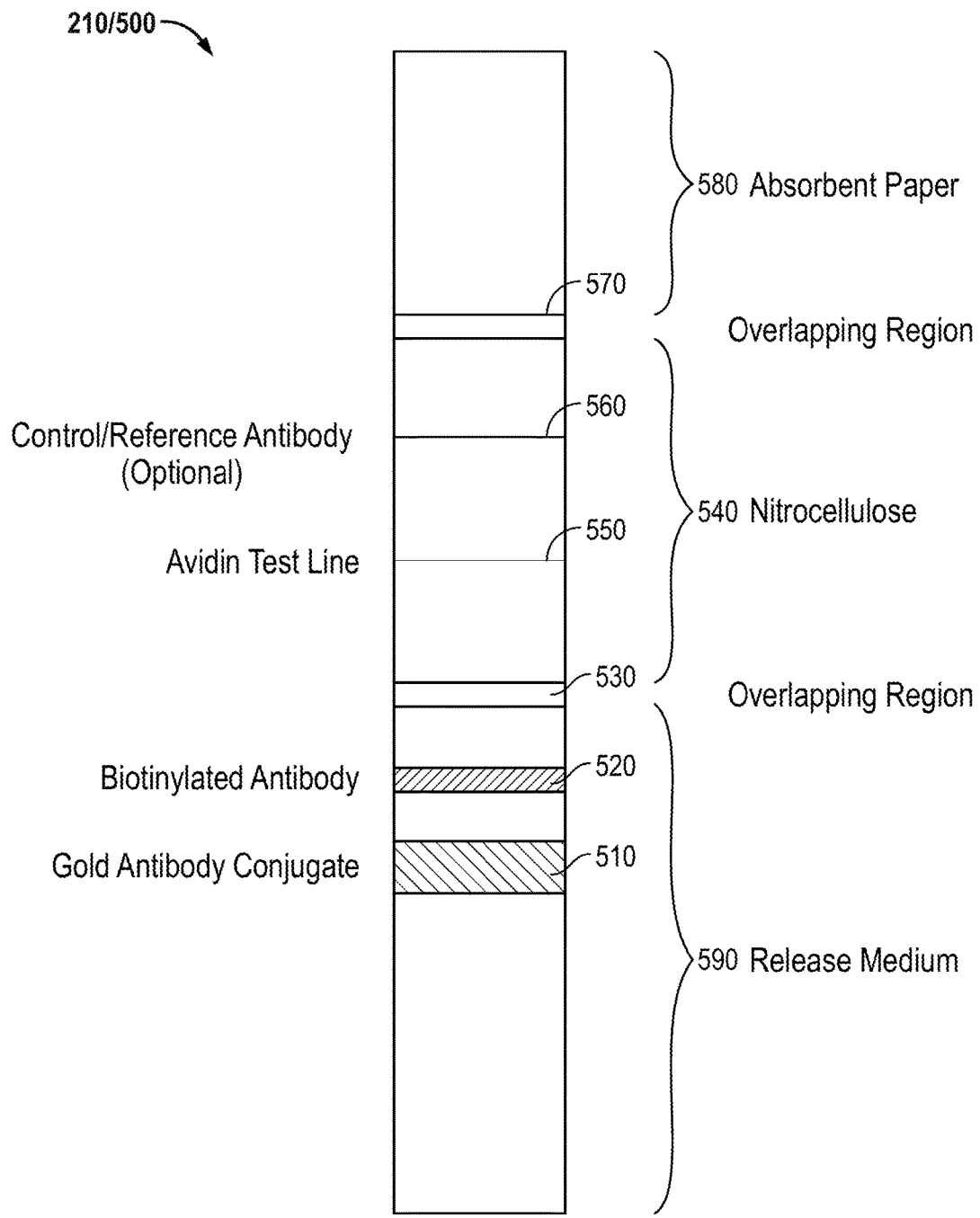
FIG. 5 is a diagram of an example of a triphasic test strip suitable for use in an implementation of the invention.

FIG. 5 is a diagram of an example of a triphasic test strip suitable for use in an implementation of the invention. However, it will be appreciated that a wide variety of test strip designs may be used. The test strip 210/500 shown in FIG. 5 may be included in device 10 shown in FIGS. 1A and 1B or included in the test stick assembly 200 shown in FIG. 2B. The fluid path along the test strip 210/500 will be discussed starting with the bottom of the figure and moving up. It will be recognized that this spatial orientation is merely a convenience. At the bottom of the test strip 210/500, a fluid sample may be applied. The test strip 210/500 may be formed from an absorbent material to aid in the uptake of the fluid sample. The fluid sample may encounter a conjugate region 510. In the example shown, the conjugate region 510 is a colloidal gold antibody conjugate region where the antibody binds to the analyte of interest (e.g., hCG). As the fluid sample passes through the conjugate region 510, analyte in the fluid sample will bind the gold conjugated antibody in the liquid phase and carry the conjugate-analyte complex along the test strip. The fluid sample may then pass through a second antibody region 520. In the example shown, the second antibody region 520 includes biotinylated antibody (antibody chemically coupled to biotin) that specifically binds to a different epitope on the analyte of interest than the gold conjugated antibody, forming a "sandwich" complex of analyte and two antibodies, one with colloidal gold, and the other with biotin. The sandwich complex may then be carried further along the test strip across a first overlapping region 530. The area from the start of the test strip 210/500 to the first overlapping region 530 may generally be referred to as the release medium 590.

After the overlapping region 530, the test strip 210/500 includes a capture medium 540. As the fluid sample continues along the test strip 210/500, the sample next encounters a test line 550. In the example shown in FIG. 5, the test line 550 is an avidin test line for binding the biotin on the second antibody to capture the sandwich complex (with the gold) at the test line. The test line 550 will thus become darker as more of the sandwich complexes are accumulated. In an example implementation where the conjugate comprises colloidal gold, the electronics system, which may include sensors and/or a processor for performing a transformative algorithm on sensed data, may measure the colloidal gold specifically bound at the test line 550 of the test strip 210/500. After the test line 550, the test strip 210/500 may include a control line 560. The control line 560 may also generally be referred to as a reference line. When present, the control line 560 includes antibodies or other proteins that specifically bind the gold conjugated antibody to provide a measurement of gold bound antibody in the fluid that is not specifically bound to the analyte. Reflectance measurements from the test line 550 and/or control/reference line 560 may be used separately to define successful testing and analyte concentrations. In some embodiments, the reflectance of light from the test line 550 may be compared with the reflectance from the test strip downstream from the test line 550 in a region where there may or may not be a control/reference line 560 to define successful testing and analyte concentrations. Test strips without a control/reference line may be advantageous because it eliminates the need for the antibodies at this line, reducing cost of the test strip.

The capture medium 540 may terminate with a second overlapping region 570. The second overlapping region 570 may serve as a border between the capture medium 540 and an absorbent portion 580 of the test strip 210/500. The absorbent portion 580 of the test strip 210/500 facilitates the uptake of the fluid sample as it arrives at the end of the test strip 210/500.

Test strips of this nature are known in the art, and are described in more detail in, for example, FIGS. 2-6 and the accompanying description of U.S. Pat. No. 6,319,676, the entire content of which is hereby incorporated by reference.

It may be desirable to align the test strip 210/500 when inserted into a digital detection device, such as the digital detection device 10 shown in FIG. 1 or the digital detection device 100 shown in FIG. 2, such that the capture medium region is substantially located under the sensor 430. A first sensor 430 may be located directly over the test line 550. A second sensor may be located directly over a second region of the test strip that may or may not contain a control/reference line. Further details of one embodiment of a sensor 430, emitter 440, and test strip 210/500 alignment are discussed below. Measurements of the reflectivities provide a measure of analyte concentration.

Figure 6:
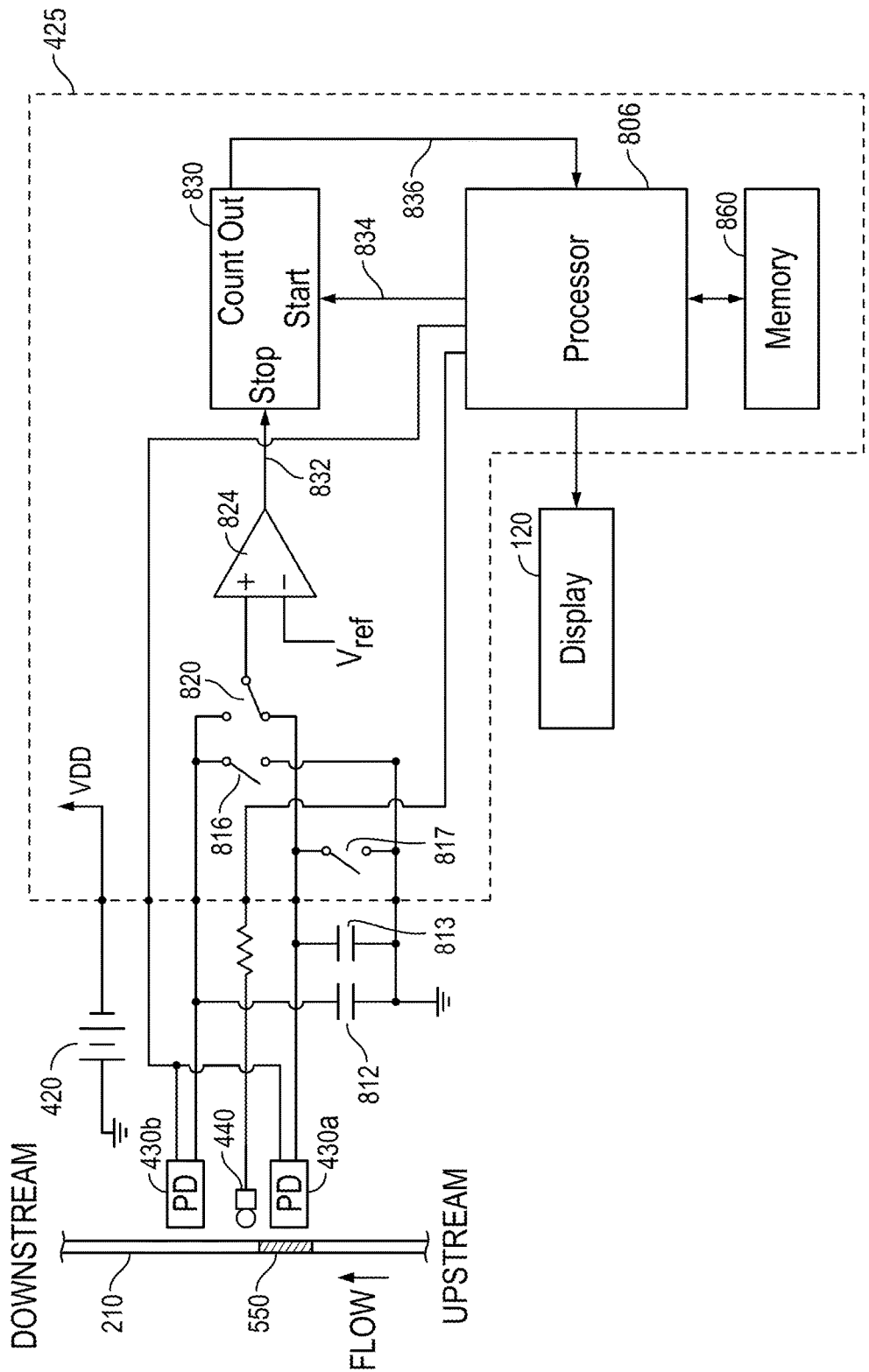
FIG. 6 is a circuit diagram of an example circuit suitable for use in a digital detection device.

FIG. 6 is a circuit diagram of an example circuit suitable for use in a digital detection device. This implementation includes photodetectors 430a and 430b as the sensors. Sensor 430a may be positioned substantially over the test line 550 of the test strip. Sensor 430b many be positioned over a blank region downstream of the test line on the test strip. In this embodiment, no control/reference line is present. As described further below, reflectance measurements are made for these two regions for a time period after a fluid sample is applied to one end of the test strip.

The circuit includes a light emitter 440. The light emitter 440 may be an LED. The light emitter 440 is connected a processing/control circuit 806 that may be in the processor chip 425. The photodetectors 430a and 430b are also each coupled to the processing/control circuit 806 to control initiation of the photodetector operation. The output of photodetector 430a is coupled to capacitor 813, and the output of photodetector 430b is coupled to capacitor 812. The other side of each capacitor is grounded. Each capacitor further has a reset switch 817 and 816 connected across it to selectively discharge the capacitors. In operation, each photodetector output will charge its respective capacitor with its output current. The time required to charge each capacitor to a defined threshold level is a measure of the photodetector output, and thus is a measure of the reflectivity of the test strip in the region under each photodetector.

The time period to charge the capacitor to the threshold may be determined as follows. If photodetector 430a is being measured, LED 440 is switched on, switch 817 is opened, a counter 830 is started, and a switch 820 is used to connect the high side of capacitor 813 to the positive input of a comparator 824. The negative input to the comparator 824 is coupled to a reference voltage, which is advantageously derived from the battery voltage VDD. For example, the reference voltage may be ½ of VDD. The output 832 of the comparator 824 is coupled to a stop input of the counter 830 that stops the counter 830 when the comparator output goes high. As capacitor 813 is charged by the photodetector 430a output, the voltage on the high side of capacitor 813 increases, increasing the voltage input to the positive input of the comparator 824. When this voltage reaches the reference voltage input to the negative side of the comparator 824, the comparator output 832 transitions from low to high. The count value 836, which is a measure of the time between counter start at the beginning of the process and counter stop when the comparator goes high, is fed to the processor 806. In this embodiment, a larger count indicates a longer time for capacitor charging, indicating a lower photodetector output, and therefore a less reflective surface under the photodetector. Once a count for photodetector 430a is acquired, the switch 817 is closed, and the process repeats for photodetector 430b, switch 816, and capacitor 812, with the switch 820 in the other position.

Collectively, the elements of the processor chip 425 are connected to one side of a power supply 420. Explicit power transmission traces between the elements of the processor chip 425 have been omitted from FIG. 6. The other side of the power supply 420 is connected to a ground. Processor chip 425 may also include a memory 860 for storing data and instructions as described above.

In operation, the digital detection device, such as the digital detection device 10 shown in FIG. 1A or digital detection device 100 shown in FIG. 2A, detects that a test strip is installed and begins taking count values for photodetector 430a (the upstream photodetector) and 430b (the downstream photodetector) at a polling rate. A rate of once per second for the polling rate has been found suitable for reasons that will be described further below. From each pair of counts, the reader computes a measurement value M defined as follows:

$$M = S^*((A/B)-(C/D)) \qquad \text{Equation 1}$$

Where A=initial downstream count value
  B=current downstream count value
  C=initial upstream count value
  D=current upstream count value
  S=constant scale factor In use of the device, immediately following test strip installation and application of a fluid sample, the value of M is near zero, because both areas of the test strip under each photodetector have approximately equal reflectances before the fluid sample migrates down the test strip to reach the photodetector regions. Furthermore, the current counts B and D will be about equal to the initial counts A and C, making M about equal to 1−1 which is near zero. When the fluid front of the sample first reaches the upstream detector, the count value D will increase because the test strip in that region becomes less reflective, causing M to increase since A/B is still near 1, but C/D is now less than 1. The reconstituted gold labeled antibodies and antibody-antigen sandwiches slightly lag the fluid front. When the gold reaches the region under the upstream photodetector, D increases further, which further increases the value for M. If antigen is present in the fluid sample, gold labeled antibody-antigen sandwiches will be captured at the test line 550, stopping their further migration down the test strip. When the fluid front and gold labeled antibodies reach the downstream photodetector region, this area will darken also, increasing the count value of B, which decreases the value for M, because A/B becomes smaller than 1. As the assay develops further, most of the gold labeled antibodies that are not part of sandwich complexes and are thus not captured at the test line 550 migrate past the downstream detector region, leaving behind a residual background. After a few minutes, the values for B and D stabilize, stabilizing the value for M to a final value. This value for M will be greater than 0 if the reflectance of the test line is lower than the reflectance of the blank region, which indicates that gold labeled antibody-antigen sandwiches captured at the test line 550 exceed the residual background of gold labeled antibodies in the blank downstream region of the test strip (because D will be larger than B). Higher final values of M indicate higher concentrations of antigen in the fluid sample.

As described above, the device does not monitor M as a continuous variable, but rather generates M values at a given polling rate, which may be approximately once per second. The actual numerical values for M that are produced with this algorithm will depend on the value selected for the scale factor S and the sensitivity of the assay materials. In one embodiment developed by the applicants, the scale factor is 666, and the resulting M values generally range from relatively small negative numbers to 100 or so.

A normal valid test has several characteristic shape features and trend features in the time course of collected calculated values (e.g., a series of calculated M values as the reagent develops on the assay test device). Conventionally, these features have been ignored in the determination of test results and test validity. Typically, only initial detections of fluid and label and final detections of bound label to the test line have been considered. Described further below are novel apparatus and methods to include these shape and trend features as part of determinations of the validity of a test and/or the result of a test.

Figure 7:
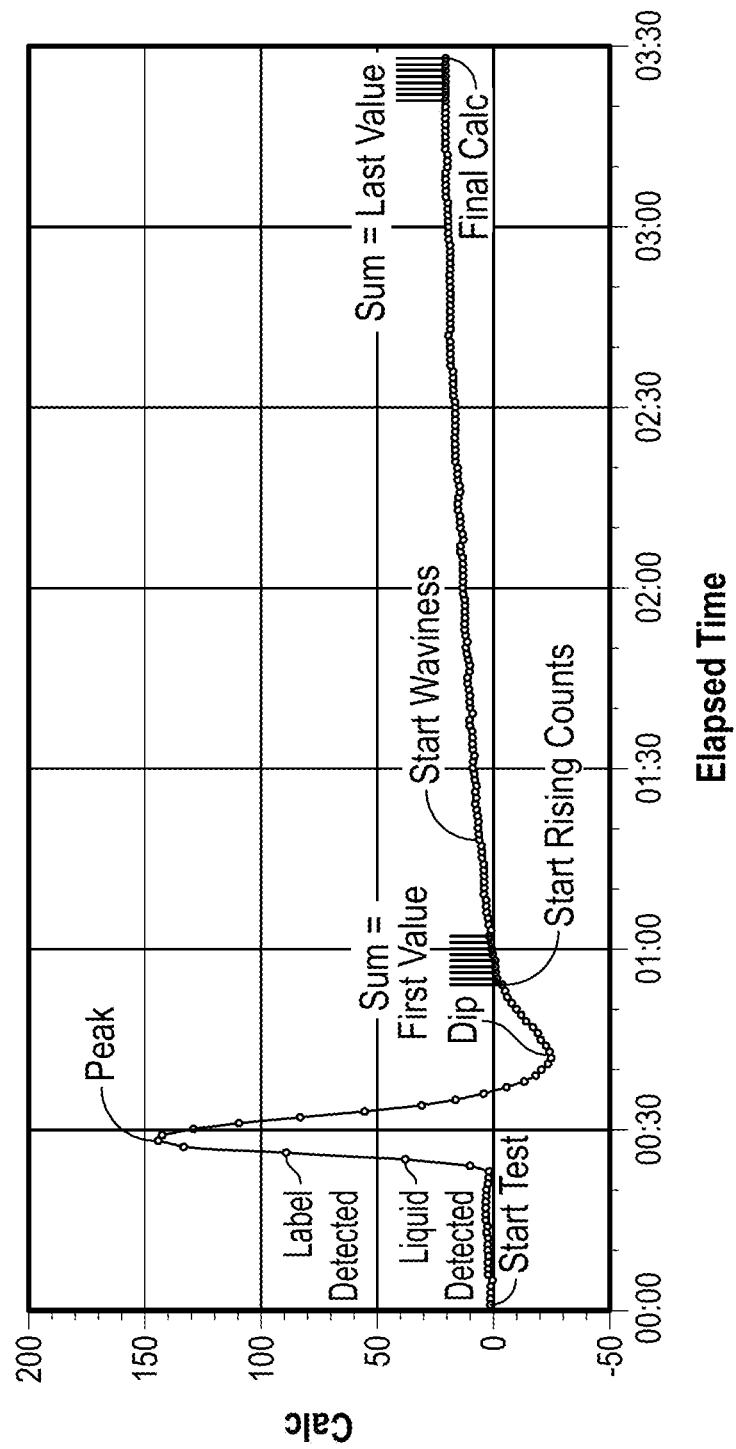
FIG. 7 shows a graph of calculated values over time for a test period.

FIG. 7 shows a graph of calculated values M over time for an assay time period for a normal, valid, and positive test result. As used herein, these M values individually or collectively are one example of a signal or signals representative of reagent development during the assay time period. As shown in FIG. 7, the M values follow a characteristic shape and trend during reagent development including an initial peak, a subsequent dip, and then a generally monotonic rise to the end of the test period. These shapes and trends may be identified and used to enhance the accuracy of test results as described further below.

The test is initiated when the device is removed from the pouch and exposed to ambient light. Upon detecting ambient light, the microcontroller wakes up and takes initial front and rear sensor readings (collectively referred to as initial reading). Subsequent readings are taken once every 1.048. A calculated value (e.g., M above) is derived from the front and rear sensors and is used to determine how much the test line area differs from the background. At the initial reading, because the test has not been performed, both front and rear sensors are detecting similar background values. The detection device may be configured to display a clock icon indicating that the test is ready to be performed. The user applies the fluid sample and waits.

When the fluid sample reaches the front sensor, the calculated value starts to rise as described above. When the calculated value first meets or exceeds a pre-determined value (e.g., 20) or above, this indicates that fluid sample has been detected. This point is indicated by the label "liquid detected" in the graph of FIG. 7. In response, a "Liquid Detected" flag may be set.

When the calculated value first meets or exceeds a second pre-determined value (e.g., 75) gold migration has been detected at the front sensor. This point is indicated by the label "label detected" in the graph of FIG. 7. The detection device may be configured to display an indication, such as now starting to blink the clock icon, to indicate this event, and a "Label Detected" flag may be set.

The algorithm now enters a loop, taking 172 sensor readings at regular intervals and computing the associated M values. In the implementation shown in FIG. 7, the interval is 1.048 seconds per reading. This takes 180 seconds, or three minutes following the data point at which the Label Detected flag was set. After three minutes the test is over and the result is determined and displayed.

After the "label detected" data point is taken, the algorithm looks for a local maximum. This peak value occurs in a normal valid test when the initial solubilized label begins to reach the rear downstream sensor. The peak is found by comparing the next calculated value with the data point of label detection. If it is higher, the time or index of this data point and its value are stored in a memory location. This continues for subsequent data points, overwriting the stored value and data point index or time each time the current value rises from the last value. When a calculated value is generated that is lower than the stored value, the difference between the new value and the stored value is computed, without overwriting the stored values. When this difference is greater than a threshold, a "Peak Found" flag may be set. In one implementation, the threshold is nine. FIG. 7 identifies the peak at the point labeled "Peak" near the 30 second mark. The data point index or time of the stored highest value after the calculated values drop more than the threshold represents the "peak time" in the course of reagent development.

Once the peak has been found, the algorithm looks for a local minimum or dip in the series of calculated values. The dip that follows the initial peak occurs in a normal valid test when the initial solubilized label begins to travel beyond the rear downstream sensor. The dip value is found by calculating the current calculated value minus the previous calculated value. If the difference is negative, the calculated value is still going down. When the difference becomes zero or goes positive, the time or data point index of the smallest calculated value is stored in memory and a "Dip Found" flag may be set. FIG. 7 identifies the dip at the point labeled "Dip" near the 45 second mark. The data point index or time of the lowest sample value represents the "dip time" in the course of reagent development.

After the dip in the calculated value is detected, the test waits for a pre-determined period of time. The time may be marked by the timer, e.g. in device 10 or device 100, or a number of additional data points collected. Once the period of time has passed (also referred to as the BEGIN_TIME), a number (e.g., 8 as shown in FIG. 7) sequential values are summed to generate a "First Value." The BEGIN_TIME may be 13 data points (e.g. 13.624 seconds) after the data point previously identified as the dip time.

Also starting at BEGIN_TIME after the dip is detected, a "rising count value" may be collected continuously for the rest of the test period. To compute this rising count value, an initial calculated value is stored. This initial value may be the 13$^{th}$ value after the dip data point index number, e.g. the sample taken at BEGIN_TIME. The next data point is compared with this stored data point. If the value associated with this next data point is larger than the stored data point value, the rising count value is incremented. If it is less than the stored data point value, the rising count value is decremented. If the values are the same, the rising count value is unchanged. The current data point value then replaces the stored data point value. The rising count value is therefore the number of times the calculated value rises minus the number of times it falls. As will be described further below, the rising count value can be compared to a limit or threshold at the end of the assay. If the rising count is high, this indicates a generally monotonic increase in reagent development at the test line.

Another parameter that may be calculated is a measure of the waviness of the reagent development between the dip time and the end of the test period. In one implementation, the detection of waviness is configured to begin 36 data points (37.728 seconds) after the detection of the dip, designated as "Start Waviness" in FIG. 7. In one implementation, an initial calculated value at the Start Waviness point may be stored in a first memory location. This value in the first memory location represents a maximum calculated value "MaxCalc." For subsequent data points, the new measurement value is compared with the value in MaxCalc. If the new measurement value is greater than the current value of MaxCalc, then MaxCalc is replaced with the new measurement value. In this way, MaxCalc always contains the maximum measured value. If the new measurement value is lower than MaxCalc, the difference between MaxCalc and the new measurement value is stored in a second memory location as a "waviness" measure. This difference represents is how far the current value of is from the stored maximum value. If this number is greater than the currently stored waviness value, then the waviness value is set to this difference. When the stored waviness value is large, this indicates the presence of at least one additional peak and dip combination that follows the first normal peak and dip combination. Such a shape is not expected to be present in a normal valid test.

Other algorithms for producing a waviness parameter are also possible. In one such implementation, each calculated value after the Start Waviness time is subtracted from the local moving average. If the calculated value falls below the moving average, this deviation is compared to the previous deviations. The largest of these deviations is saved in memory.

Near the end of the test period, the last eight sequential calculated values are added together to give a quantity called "Last Value." Furthermore, the First Value may be subtracted from the Last Value to derive a "total rise value" representative of the total change in reagent development that occurred after the dip which is after the initial fluid and solubilized label fronts have passed the two sensors. As will be described further below, this total rise parameter can be compared to a threshold. When the total rise exceeds the threshold, this indicates significant development at the test line over the course of the assay.

The above description of FIG. 7 illustrates several novel parameters for characterizing reagent development during the course of an assay. Some of these parameters, denoted here as reagent development trend shape parameters, may involve identifying local maximums, minimums, or both in the course of the assay. These can be useful in determining whether an assay can be considered to have produced a valid, reliable final result. This is described below with reference to FIGS. 8 and 9.

Figure 8:
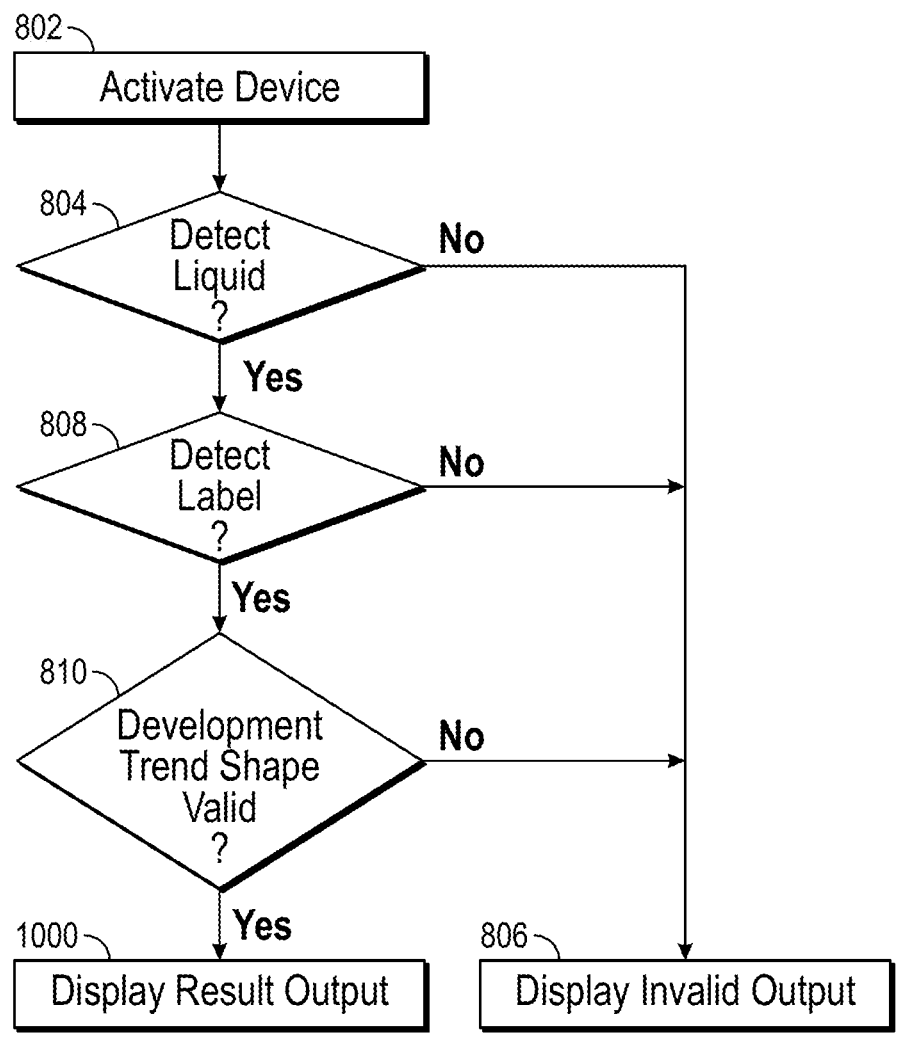
FIG. 8 is a flow diagram of a process for detecting an invalid test for a monitored analyte.

FIG. 8 is a flow diagram of an exemplary process for detecting a valid test for a monitored analyte. At block 802, the device is activated as described above. At decision block 804, it is determined whether the fluid sample has been detected. As described above, the fluid sample may be detected using several processes. The fluid sample may fail to be detected if the calculated value never reaches a pre-determined value (e.g., 20) for a pre-determined period of time (e.g., three minutes). If the fluid sample is not detected, an indication of an invalid test is transmitted, such as via a display, at block 806.

If the fluid sample is detected, at decision block 808, it is determined whether the label particles used in the test have been detected. In an implementation described above, the label particles used in the test are gold particles. It will be appreciated that the process shown in FIG. 8 may be applied for any label particles. Detection of the label particles may be accomplished by generating a calculated value above a second threshold (e.g., 75) as described above. If label particles are not detected, an indication of an invalid test is transmitted, such as via a display, at block 806.

If label particles are detected, at decision block 810, the shape of the development trend of the calculated values is assessed. One assessment is to identify the presence or absence of local minima and maxima in portions of the development trend of the calculated values. As discussed above, the presence of one or more of an initial peak, a subsequent dip, and a further subsequent absence of excessive waviness may be detected. If the development trend shape is invalid, an indication of an invalid test is transmitted, such as via a display, at block 806. If the development trend shape is valid, at block 1000, the output of the test result is transmitted, such as via a display. Generating the output of the test result will be described in further detail in reference to FIG. 10.

Figure 9:
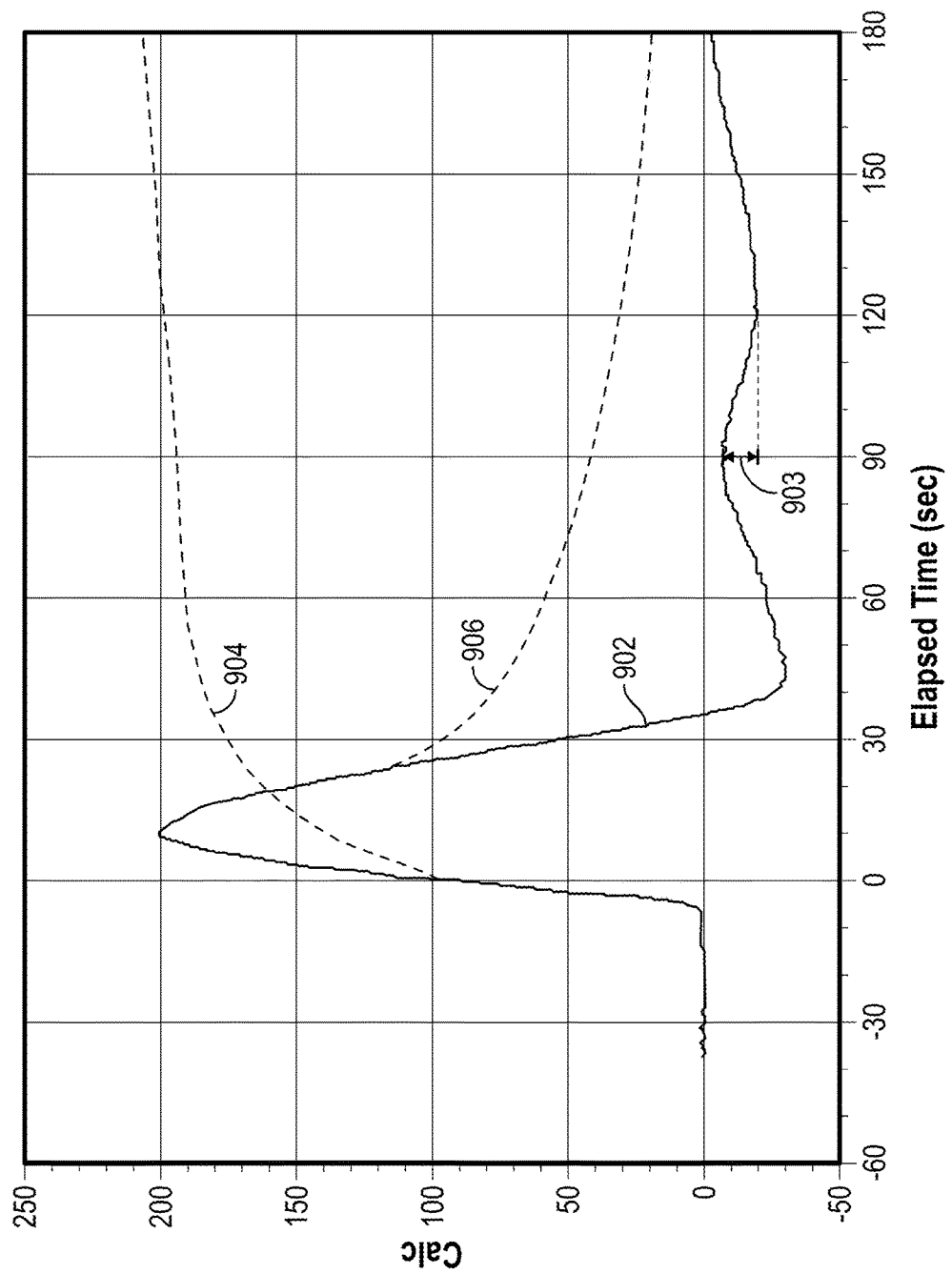
FIG. 9 shows sample graphs of calculated values over time for a test period for invalid tests.

Detecting a trend shape of reagent development is illustrated further in FIG. 9, which contains sample graphs of calculated values over time for a test period for invalid tests. The graph shows calculated values on the y-axis and elapsed test time along the x-axis. Time 0 is the time indicating the start of the test. The graph includes a main plot of calculated values in solid line, plot 902. This main plot illustrates an invalid test due to waviness. In this example, after the first dip, at approximately time 90 seconds, a local maximum in calculated values is present. After this, at approximately time 120 seconds, a local minimum is present. The difference between these two values will be stored as the waviness value described above. If this difference 903 exceeds a threshold, the test may be identified as invalid due to excessive waviness.

Plot 904 shows a graph of calculated values which departs from the main plot at shortly after time 0. Plot 904 illustrates an example of a failure to detect an initial local maximum within three minutes. As is shown by Plot 904, no peak is reached for the calculated values plotted by the end of the test period, which in FIG. 9 is 180 seconds.

Plot 906 shows another graph of calculated values which departs from the main plot shortly after time 20. Plot 906 illustrates an example of a failure to detect a local minimum subsequent to the initial peak. As can be seen in plot 906, the calculated values peak at 200 at approximately 10 seconds. The calculated values then drop off gradually, but never exhibit a dip such as that shown in the main plot 902 at approximately 40 seconds. In this case, the test would be identified as invalid.

The above description of FIG. 7 also illustrates several novel parameters, denoted here as reagent development trend parameters, which may involve identifying a general monotonic trend of sufficient magnitude in reagent development in the course of the assay. After an assay is determined to be valid using the reagent development trend shape parameters as described above, these other parameters can be useful in determining the test result output that is displayed to the user of the device. This is described below with reference to FIGS. 10, 11, and 12.

Figure 10:
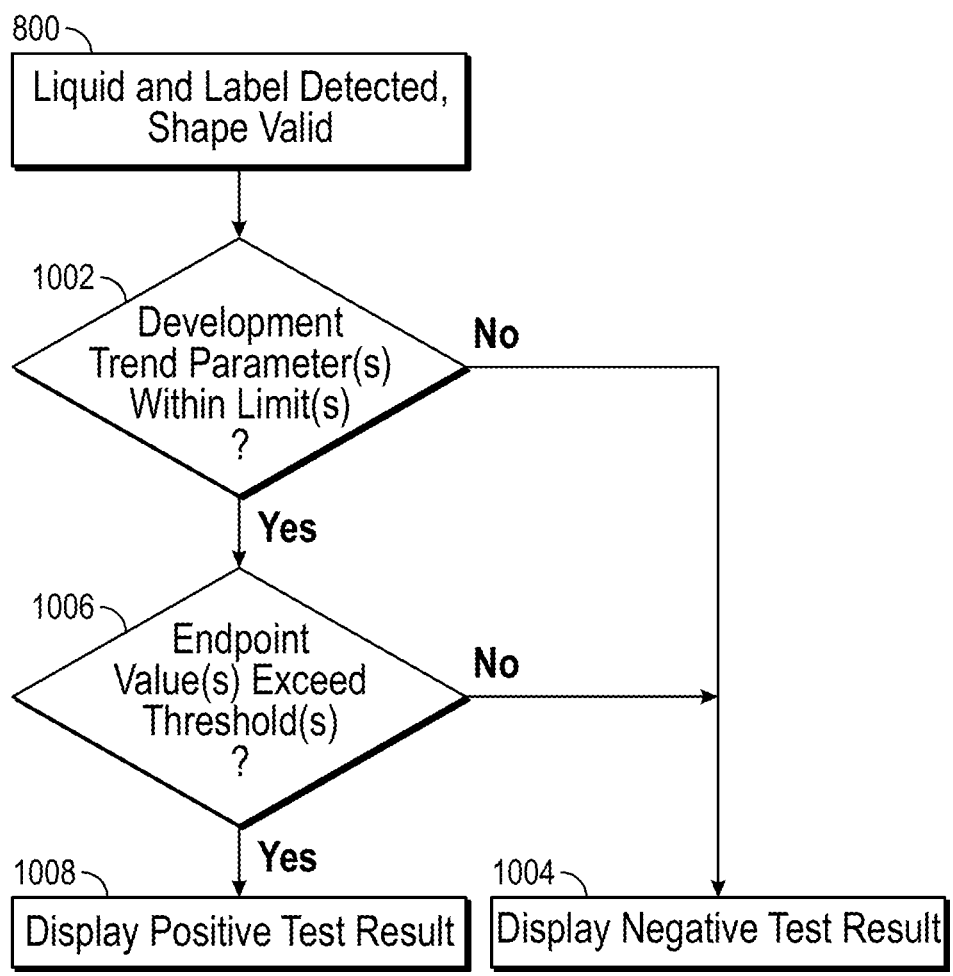
FIG. 10 is a flow diagram of a process for deriving a positive or negative test result output for a monitored analyte.

FIG. 10 is a flow diagram of an exemplary process for detecting a monitored analyte. The flow begins at block 800 where the validity of the fluid sample, label, and development trend are affirmed as described in FIG. 8. At decision block 1002, a determination is made as to whether one or more of the development trend parameters are within pre-determined limits. Development trend parameters may include the rising count and total rise as described above. If the development trend parameters are not within the pre-determined limits, at block 1004, a negative test result is indicated, such as via a display, indicating that the analyte is not present in the fluid sample. Example plots of calculated values producing a negative test result are shown and described in further detail below with reference to FIG. 12.

If the development trend parameters are within the pre-determined limits, at decision block 1006, a determination is made as to whether one or more of the endpoint values exceed pre-determined thresholds. The endpoint values may include the Last Value and/or the Final Calc value of FIG. 7. If the endpoint parameters do not exceed the pre-determined thresholds, at block 1004, a negative test result is indicated, such as via a display. If the endpoint value(s) exceed the pre-determined thresholds, at block 1008, a positive test result is indicated, such as via a display. An example plot of calculated values for a positive test result indicating the presence of the analyte are shown and described in further detail below with reference to FIG. 11. In some implementations, the indication of the test result at block 1004 and/or block 1008 may include transmitting a signal including the test result for further processing (e.g., storage, transmission).

As described in reference to FIG. 10, development trend parameters are determined as "within limits." It will be appreciated that in some implementations, the determination of block 1002 may include identifying whether the development trend parameters exceed and/or fall below a pre-determined value. Similarly, while the determination of block 1006 is performed to determine if endpoint values exceed a threshold, it will be appreciated that in some implementations, the determination of block 1002 may include identifying whether the endpoint values are within a pre-determined range of values and/or fall below a pre-determined value.

Figure 11:
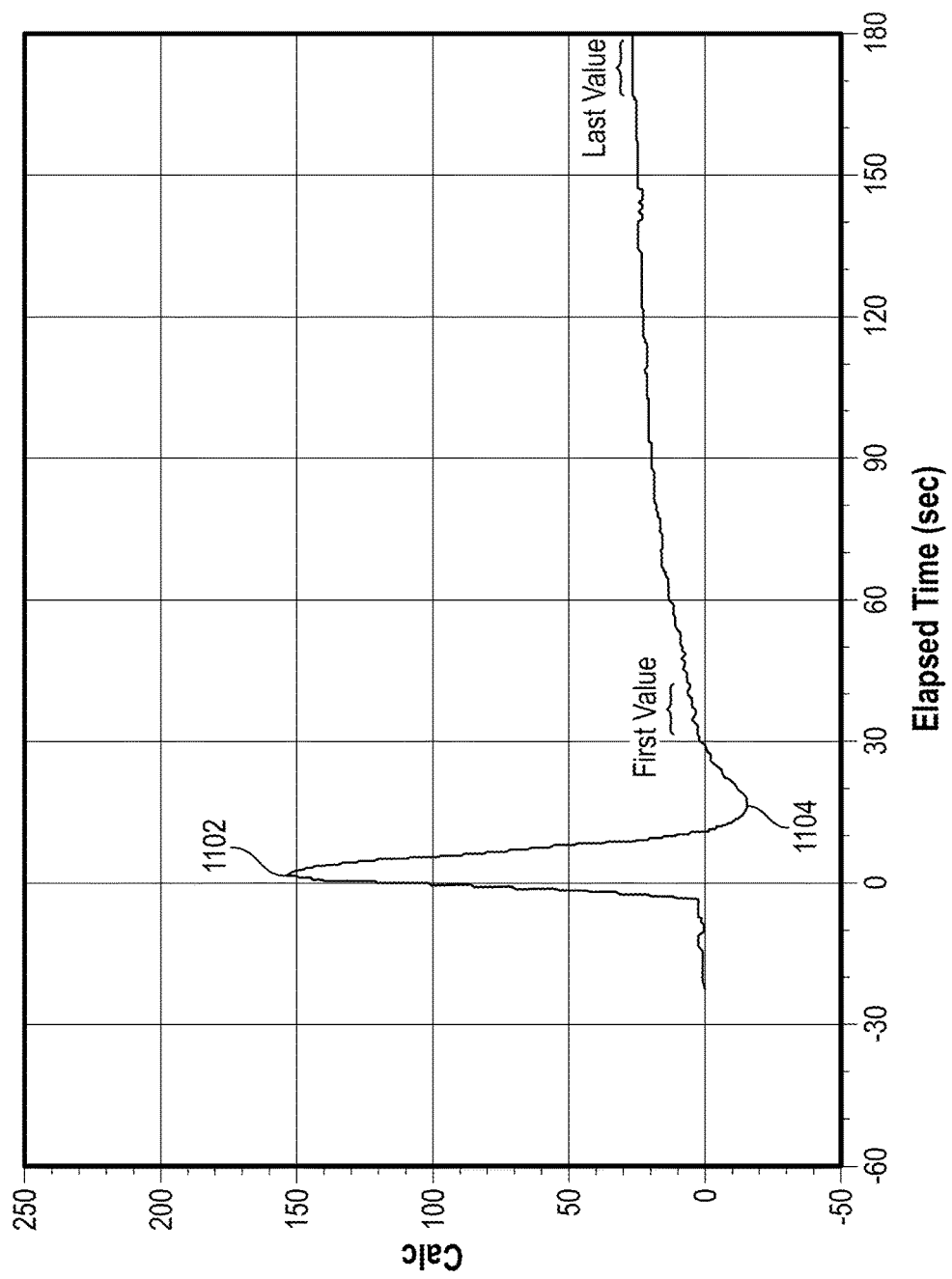
FIG. 11 shows a sample graph of calculated values producing a positive test output.

FIG. 11 shows an example plot of calculated values over time for a positive test result. The graph shows calculated values on the y-axis and elapsed test time along the x-axis. In this example, an initial peak 1102 and an initial dip 1104 will be detected, and the subsequent trend does not show a wavy shape, so the test will be considered valid. The development subsequent to the dip 1104 rises monotonically, so the rising count value described above will be above the required threshold. The total rise is sufficient to exceed the total rise threshold. In addition, the endpoint values are large enough to exceed the endpoint threshold. Because the development trend parameters and the endpoint parameter both exceed the required thresholds, a positive result is output.

Figure 12:
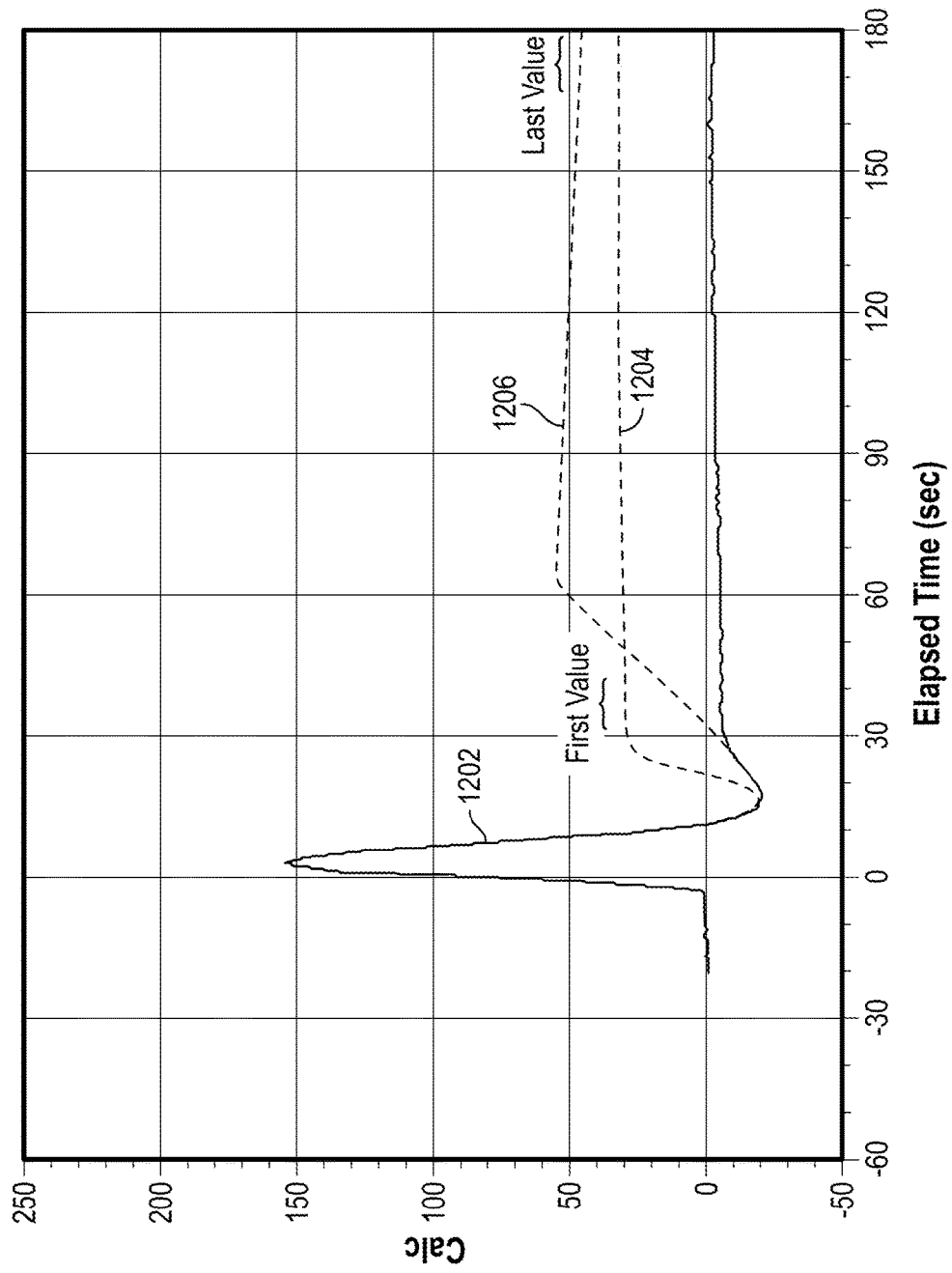
FIG. 12 shows sample graphs of calculated values producing a negative test output.

FIG. 12 shows example plots of calculated values over time for negative test results. The main plot 1202 illustrates a typical reagent development for a negative result. Following the dip, the calculated values rise very little, and the final calculated value(s) are low. For example graph 1204, however, the final values are relatively high. Conventionally, this might produce a positive test result. However, the fact that the total rise from First Value to Last Value is small, this indicates that the reason for the relatively large final value is likely unrelated to the presence of the analyte. In some embodiments, the total rise parameter will therefore be below the threshold, and a negative output will be displayed instead, which is a more accurate result. In plot 1206, both the Last Value and the total rise are large, but the curve shows decreasing calculated values over most of the development period after the First Value. This drop is not consistent with analyte bound reagent slowly developing at the test region. This will be detected by the rising count parameter, which will not exceed the threshold for this plot. Therefore, a negative output will be displayed, which again is a more accurate result than a conventional test that simply looks at the last calculated value or values.

It will be appreciated that the above described system could be used to detect analytes other than hormones, with especially advantageous application in any environment where samples are collected, and the diagnostic test may be interpreted according to a photosensitive reading. For example, variation of the monitored analyte may be used to indicate an onset of menopause (e.g., natural menopause, perimenopause, induced menopause, premature menopause, or post menopause) or ovarian reserve for the individual. In an implementation, variation of a monitored analyte such as progesterone may be used to indicate an onset of an abnormal pregnancy (e.g., failed implantation, ectopic pregnancy) for the individual. In an example progesterone implementation, a normal pregnancy is detected if the progesterone level is greater than the threshold value while levels equal to or less than the threshold indicate an abnormal or failing pregnancy. The detection method or device may be included in a test kit such as an ovulation detector test kit sensing luteinizing hormone (LH) in urine samples from an individual.

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various operations of methods described above may be performed by any suitable means capable of performing the operations, such as various hardware and/or software component(s), circuits, and/or module(s). Generally, any operations illustrated in the Figures may be performed by corresponding functional means capable of performing the operations.

The various illustrative logical blocks, modules and circuits described in connection with the present disclosure may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

In one or more aspects, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Thus, in some aspects computer readable medium may comprise non-transitory computer readable medium (e.g., tangible media). In addition, in some aspects computer readable medium may comprise transitory computer readable medium (e.g., a signal). Combinations of the above should also be included within the scope of computer-readable media.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

The functions described may be implemented in hardware, software, firmware or any combination thereof. If implemented in software, the functions may be stored as one or more instructions on a computer-readable medium. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray® disc where disks usually reproduce data magnetically, while discs reproduce data optically with lasers.

Thus, certain aspects may comprise a computer program product for performing the operations presented herein. For example, such a computer program product may comprise a computer readable medium having instructions stored (and/or encoded) thereon, the instructions being executable by one or more processors to perform the operations described herein. For certain aspects, the computer program product may include packaging material.

Software, instructions, or data may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a device can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the claims.

While the foregoing is directed to aspects of the present disclosure, other and further aspects of the disclosure may be devised without departing from the basic scope thereof, and the scope thereof is determined by the claims that follow.

What is claimed is:

1. A test kit for detecting an analyte in a fluid sample, the test kit comprising:
a reader, the reader comprising:
an assay test device or a port for accepting an assay test device therein; and
a circuit configured to:
generate a signal representative of reagent development during an assay time period;
generate at least one reagent development trend signal during at least a portion of the assay time period, wherein the at least one reagent development trend signal comprises a measure of consistent unidirectional change in reagent development;
generate at least one endpoint signal representative of a final reagent development condition at or near the end of the assay time period;

determine whether the at least one reagent development trend signal is within a pre-determined limit;

determine whether the at least one endpoint signal exceeds a pre-determined threshold;

select a positive test result when both the at least one reagent development trend signal is within a pre-determined limit and when the at least one endpoint signal exceeds a pre-determined threshold and select a negative test result when either the at least one reagent development trend signal is not within a pre-determined limit or when the at least one endpoint signal does not exceed a pre-determined threshold; and output a test result.

2. The test kit of claim 1, wherein the assay test device is configured to receive a fluid sample.

3. The test kit of claim 1, wherein the analyte is selected from a group comprising follicle stimulating hormone, thyroid stimulating hormone, luteinizing hormone, human chorionic gonadotropin, estrogen, progesterone, testosterone, or metabolites thereof.

4. A test kit for detecting an analyte in a fluid sample, the test kit comprising:

a reader, the reader comprising:

an assay test device or a port for accepting an assay test device therein; and a circuit configured to:

generate a signal representative of reagent development during an assay time period;

generate at least one reagent development trend signal during at least a portion of the assay time period, wherein the at least one reagent development trend signal is based at least in part on differences between the signal representative of reagent development at different times during the at least a portion of the assay time period;

generate at least one endpoint signal representative of a final reagent development condition at or near the end of the assay time period;

determine whether the at least one reagent development trend signal is within a pre-determined limit;

determine whether the at least one endpoint signal exceeds a pre-determined threshold;

select a positive test result when both the at least one reagent development trend signal is within a pre-determined limit and when the at least one endpoint signal exceeds a pre-determined threshold and select a negative test result when either the at least one reagent development trend signal is not within a pre-determined limit or when the at least one endpoint signal does not exceed a pre-determined threshold; and output a test result.

5. The test kit of claim 4, wherein the at least one reagent development trend signal comprises at least one of a rising count value and a total rise value.

6. The test kit of claim 5, wherein the rising count value is generated by:

counting periods of increase in the signal representative of reagent development during the at least a portion of the assay time period;

counting periods of no increase and decrease in the signal representative of reagent development during the at least a portion of the assay time period; and comparing the count of periods of increase and the count of periods of no increase and decrease in the signal representative of reagent development during the at least a portion of the assay time period.

7. The test kit of claim 6, wherein the circuit is configured to generate a positive test result indicating analyte detection if the rising count value is equal to or greater than a rising count threshold value and if the at least one endpoint signal is equal to or greater than an endpoint threshold value.

8. The test kit of claim 6, wherein the circuit is configured to generate a negative test result indicating no analyte detection if the rising count value is less than a rising count threshold value or if the at least one endpoint signal is less than an endpoint threshold value.

9. A test kit for detecting an analyte in a fluid sample from an individual, the test kit comprising:

a reader, the reader comprising:

an assay test device or a port for accepting an assay test device therein; and a circuit configured to:

generate a signal representative of reagent development during an assay time period;

search the signal representative of reagent development for both a local maximum and a local minimum;

generate at least one reagent development trend shape signal based at least in part on results of the search for both a local maximum and a local minimum in the signal representative of reagent development during at least a portion of the assay time period, wherein the at least one reagent development trend shape signal comprises a numerical measure of deviations in an amplitude of the signal representative of reagent development during the at least a portion of the assay time period; and generate an invalid test output based at least in part on the reagent development trend shape signal.

10. The test kit of claim 9, wherein the numerical measure comprises a measure of the difference between a local maximum and a local minimum value of the signal representative of reagent development during the at least a portion of the assay time period.

11. The test kit of claim 9, wherein the circuit is configured to generate an invalid test output when the numerical measure is equal to or greater than a threshold.

12. The test kit of claim 9, wherein the reagent development trend shape signal identifies a local maximum or local minimum in the signal representative of reagent development during the at least a portion of the assay time period.

13. The test kit of claim 9, wherein the circuit is configured to generate an invalid test output if no local minimum is found after an initial local maximum.

14. The test kit of claim 9, wherein the analyte is selected from a group comprising follicle stimulating hormone, thyroid stimulating hormone, luteinizing hormone, human chorionic gonadotropin, estrogen, progesterone, testosterone, or metabolites thereof.

15. A test kit for detecting an analyte in a fluid sample from an individual, the test kit comprising:

a reader, the reader comprising:

an assay test device or a port for accepting an assay test device therein; and a circuit configured to:

generate a signal representative of reagent development during an assay time period;

search the signal representative of reagent development for both a local maximum and a local minimum;

generate at least one reagent development trend shape signal based at least in part on results of the search for both a local maximum and a local minimum in the signal representative of reagent development during at least a portion of the assay time period, wherein the at least one reagent development trend shape signal comprises a measure of the difference between an average value and a minimum value of the signal representative of reagent development during the at least a portion of the assay time period; and generate an invalid test output based at least in part on the reagent development trend shape signal.

* * * * *